United States Patent [19]

Phelps et al.

[11] Patent Number: 5,206,334
[45] Date of Patent: Apr. 27, 1993

[54] BRANCHED POLYCARBONATE FROM 2',4,4''-M-TERPHENYLTRIOL

[75] Inventors: Peter D. Phelps, Schenectady; James L. Spivack, Cobleskill, both of N.Y.

[73] Assignee: General Electric Company, Schenectady, N.Y.

[21] Appl. No.: 888,072

[22] Filed: May 26, 1992

Related U.S. Application Data

[60] Continuation-in-part of Ser. No. 797,755, Nov. 25, 1991, which is a division of Ser. No. 703,324, May 20, 1991, Pat. No. 5,105,025, which is a division of Ser. No. 632,888, Dec. 24, 1990, Pat. No. 5,049,498.

[51] Int. Cl.$^5$ .............................................. C08G 64/04
[52] U.S. Cl. .................................... 528/204; 528/196
[58] Field of Search ................................. 528/204, 196

[56] References Cited

U.S. PATENT DOCUMENTS 5,049,498  9/1991  Spivack et al. .
5,105,025  4/1992  Spivack et al. .

Primary Examiner—Harold D. Anderson
Attorney, Agent, or Firm—William H. Pittman

[57] ABSTRACT

Branched polycarbonates are prepared by the use as a branching agent, in an interfacial polycarbonate formation reaction, of a 2',4,4''-m-terphenyltriol, preferably the unsubstituted compound. Said branched polycarbonates have properties which are advantageous for blow molding and the like.

5 Claims, No Drawings

BRANCHED POLYCARBONATE FROM 2',4,4''-M-TERPHENYLTRIOL

This application is a continuation-in-part of copending application Ser. No. 07/797,755, filed Nov. 25, 1991, which is a division of Ser. No. 07/703,324, filed May 20, 1991, now U.S. Pat. No. 5,105,025, which in turn is a division of application Ser. No. 07/632,888, filed Dec. 24, 1990, now U.S. Pat. No. 5,049,498.

This invention relates to the preparation of branched polycarbonates, and particularly to their preparation with the use of a specific class of branching agents.

Branched polycarbonates have viscosity properties which make them superior to linear polycarbonates for certain applications such as blow molding. They are characterized by a higher viscosity than that of linear polycarbonates under low shear conditions, accompanied by viscosities similar to those of the unbranched polymers at higher shear. This combination of properties is often referred to as high melt strength.

Various methods for preparing branched polycarbonates are known. They typically involve the conventional interfacial method for polycarbonate preparation, wherein a dihydroxyaromatic compound undergoes reaction with phosgene in the presence of a catalyst, typically a trialkylamine, and a basic reagent as an acid acceptor. The methods differ in the branching agent used. Most branching agents are relatively expensive compounds such as trimellitic acid trichloride and 1,1,1-tris(4-hydroxyphenyl)ethane. It is therefore desirable to provide alternative branching agents.

The present invention is based on the discovery that 2',4,4''-m-terphenyltriols serve as excellent branching agents in polycarbonate synthesis. These terphenyltriols may be obtained by the action of certain strains of the fungus *Aspergillus parasiticus* (hereinafter sometimes "*A. parasiticus*") on 2'-hydroxy-m-terphenyls.

Accordingly, the invention is directed to branched polycarbonates comprising structural units of the formula

wherein $R^1$ is a divalent organic radical, and branching units of the formula

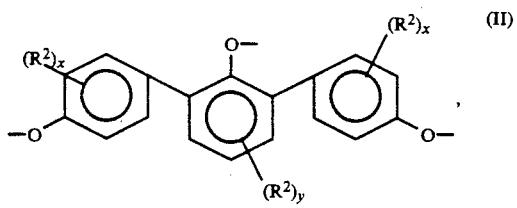

wherein each $R^2$ is a substantially inert substituent, x is 0–4 and y is 0–3.

Suitable $R^1$ values in formula I include ethylene, propylene, trimethylene, tetramethylene, hexamethylene, dodecamethylene, 1,4-(2-butenylene), 1,10-(2-ethyldecylene), 1,3-cyclopentylene, 1,3-cyclohexylene, 1,4-cyclohexylene, m-phenylene, p-phenylene, 4,4'-biphenylene, 2,2-bis(4-phenylene)propane, benzene-1,4-dimethylene (which is a vinylog of the ethylene radical and has similar properties) and similar radicals such as those which correspond to the dihydroxy compounds disclosed by name or formula (generic or specific) in U.S. Pat. No. 4,217,438, the disclosure of which is incorporated by reference herein. Also included are radicals containing non-hydrocarbon moieties. These may be substituents such as chloro, nitro, alkoxy and the like, and also linking radicals such as thio, sulfoxy, sulfone, ester, amide, ether and carbonyl. Most often, however, all $R^1$ radicals are hydrocarbon radicals.

Preferably at least about 60% and more preferably at least about 80% of the total number of $R^1$ values in the cyclic oligomer mixtures, and most desirably all of said $R^1$ values, are aromatic. The aromatic $R^1$ radicals preferably have the formula

wherein each of $A^1$ and $A^2$ is a monocyclic divalent aromatic radical and Y is a bridging radical in which one or two atoms separate $A^1$ from $A^2$. The free valence bonds in formula II are usually in the meta or para positions of $A^1$ and $A^2$ in relation to Y.

In formula III, the $A^1$ and $A^2$ values may be unsubstituted phenylene or substituted derivatives thereof, illustrative substituents (one or more) being alkyl, alkenyl, halo (especially chloro and/or bromo), nitro, alkoxy and the like. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ from $A^2$. It is most often a hydrocarbon radical and particularly a saturated radical such as methylene, cyclohexylmethylene, 2-[2.2.1]bicycloheptylmethylene, ethylene, isopropylidene, neopentylidene, cyclohexylidene, cyclopentadecylidene, cyclododecylidene or adamantylidene, especially a gemalkylene (alkylidene) radical. Also included, however, are unsaturated radicals and radicals which contain atoms other than carbon and hydrogen; for example, 2,2-dichloroethylidene, carbonyl, phthalidylidene, oxy, thio, sulfoxy and sulfone. For reasons of availability and particular suitability for the purposes of this invention, the preferred radical of formula III is the 2,2-bis(4-phenylene)propane radical, which is derived from bisphenol A and in which Y is isopropylidene and $A^1$ and $A^2$ are each p-phenylene.

The branching units have formula II in which the $R^2$ radicals represent substituents which are substantially inert under the conditions of polycarbonate preparation. Illustrative substituents are chloro, bromo and lower alkyl (i.e., alkyl of up to 7 carbon atoms), especially methyl. In the preferred branching units, however, x and y are each 0 and thus no substituents are present.

It is apparent that the branching units are derived from the aforementioned 2',4,4''-m-terphenyltriols. Compounds of this class are sometimes simply designated "m-terphenyltriols" hereinafter. The preferred unsubstituted compound is similarly designated "m-terphenyltriol".

Such m-terphenyltriols may be prepared by microbiological oxidation of the corresponding 2'-hydroxy-m-terphenyls by the action of *A. parasiticus*. Many strains of *A. parasiticus*, however, have as a drawback a tendency to produce aflatoxins, which act as potent carcinogens and mutagens during bioconversion. Preferably, therefore, a strain of *A. parasiticus* having a decreased tendency to produce aflatoxins is employed. Still more preferably, the m-terphenyltriol is prepared by a process which includes slow addition of a carbon source, as explained hereinafter.

The medium in which the *A. parasiticus* is preferably cultivated includes a carbon source, a nitrogen source and deionized water. Suitable carbon sources include glucose, maltose and fructose, with glucose generally being preferred. Readily available forms of glucose such as corn syrup are particularly useful.

As nitrogen sources, such commonly empolyed materials as ammonium salts, corn steep liquor, peptone, neopeptone, soytone, tryptone and soybean powder may be employed. Corn steep liquor is particularly suitable and is generally preferred.

The culture medium can also contain various trace elements. These are generally conventional in nature, and include boron, copper, zinc, magnesium, iron, manganese and cobalt. They may be furnished in the form of readily available compounds.

The usual method of growing *A. parasiticus* involves a rich medium containing both carbon and nitrogen sources, in which the fungal spores are germinated and grown for about 24 hours. The resulting culture is used to inoculate a larger batch of medium, also for about 24 hours. At the end of this time, near-maximum cell density has been achieved and the available carbon and nitrogen are nearly depleted. This portion of the biochemical process is sometimes hereinafter designated the "growth phase". The compound to be hydroxylated, in the present case the 2'-hydroxy-m-terphenyl, is then added and undergoes oxidation in what is hereinafter termed the "bioconversion phase".

It has been discovered that when all the carbon source and nitrogen source are introduced at the beginning of the growth phase, the ammonium ion concentration of the system increases during the bioconversion phase from a value near zero at the beginning thereof. Concurrently, the pH of the system increases. When the ammonium ion concentration exceeds about 300 ppm., the conversion of 2'-hydroxy-m-terphenyl to triols ceases.

It has further been discovered that the bioconversion phase can be prolonged if carbon source is added gradually during said phase. One effect of such gradual addition is to maintain the ammonium ion concentration at a low level. The rate of pH increase is concomitantly retarded.

It is believed that the effect of gradual addition of carbon source during the bioconversion stage is based on the property of *A. parasiticus* to undergo different metabolic processes in various life stages. Thus, such gradual addition keeps the organism in the metabolic state in which the desired bioconversion takes place, while an increase in ammonium ion concentration is a signal that the organism is leaving this metabolic state. The concentration of ammonium ion in the system can be used as an index of the proper rate of addition of the carbon source. If the rate of addition is too high, the bioconversion stops, most likely because of catabolite repression.

Thus, it is well within the state of the art to regulate the addition rate of the carbon source to obtain optimum results. Both constant and variable addition rates may be employed. Suitable addition rates are often in the range of about 0.001-1.0, preferably about 0.05-0.5 and most preferably about 0.1 gram/liter/hour.

The pH of the culture medium may vary from about 3.5 to about 9 and preferably from about 5.5 to about 7. It is often convenient to buffer the pH in this range by employing as a nitrogen source corn steep liquor or a peptone, which contain buffering amino acids, or by acid or base addition. Cultivation temperatures of the *A. parasiticus* are typically in the range of about 20°-40° C. and preferably about 30°-37° C.

The 2'-hydroxy-m-terphenyl to be oxidized may be introduced into the culture medium neat (i.e., in the absence of solvent) or in a suitable solvent which is non-toxic to the microorganism. Methanol and ethanol are illustrative of such solvents.

In a preferred embodiment, the substrate is added as a fine aqueous dispersion, allowing for the addition of large amounts of substrate with maximum available surface area for interaction with the microorganism and further avoiding the inhibition of microorganism growth and activity which may occur with even low concentrations of organic solvents. Such dispersions can be easily prepared; for example, by high-shear stirring of the molten substrate at temperature above the melting point thereof with gelatin as an emulsifying agent, followed by cooling to ambient temperature with continued stirring. Using such a technique, substrate particle size can be reduced to less than 10 microns.

Additionally, as an alternative to preparing a fine dispersion of the substrate, such substrate can be admixed or dispersed in a surfactant before addition to the culture medium. Generally such surfactants are useful in amounts in the range of about 0.1-0.6% by weight of the culture medium-reaction mixture.

Examples of suitable surfactants include polyoxyethylene octylphenyl ether, available as Noniodet P40, Triton X-100 and Igepal CA. The formula of these materials is 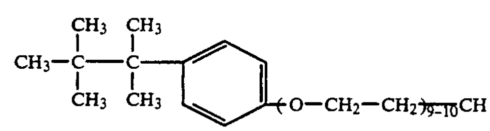 Additional examples of surfactants are polyoxyethylene (20) acetyl ether and polyoxyethylene (4) lauryl ether, available as Brij, 58 and 30, respectively; polyoxyethylene nonylphenyl ether, available as Igepal CO; and polyoxyethylene (20) sorbitan monolaurate, polyoxyethylene (20) monooleate and polyoxyethylene (20) sorbitan monopalmitate, available as Tweens, 20, 80 and 40, respectively. The presence of such surfactants in the culture medium containing microorganism and the reactant/substrate is believed to maximize microorganism-substrate contact by enhancing solubility of the sparsely water-soluble substrate. The presence of a surfactant has been found to substantially increase product concentration.

The concentration of the *A. parasiticus* required to produce the m-terphenyltriol is typically about 1-2% by weight (dry), particularly in the case of *A. parasiticus* grown on corn steep liquor.

The mutant strain of *A. parasiticus* which has reduced tendency to produce aflatoxins has been deposited with the American Type Culture Collection in Rockville, MD, on Oct. 16, 1990, as ATCC 74022. It has been found to give results in the hydroxylation of biphenyl and m-terphenyl compounds including 2'-hydroxy-m-terphenyl which compare favorably to the results obtained using the wild type *A. parasiticus*. For comparative studies see Biosynthesis of p-Hydroxylated Aromatics by Joseph J. Salvo et al., *Biotechnol. Prog.*, 6, 193–197 (1990), the disclosure of which is hereby incorporated by reference.

Aflatoxin minus strains of *A. parasiticus* have been generated in the past by standard UV or chemical mutagenesis techniques. The techniques are described by Bennett, J. W.; Papa, E. D., Genetics of Aflaxtoxigenic Aspergillus Species, in *Advances in Plant Pathology*; Sidhu, G. S., Ed.; *Genetics of Pathogenic Fungi*, Vol. 6; Academic Press: London, 1988; pp. 263–280, which disclosure is hereby incorporated by reference.

The method of creating a mutant strain of *A. parasiticus* which produces less aflatoxins than an aflatoxin producing wild type of *A. parasiticus* comprises treating the spores of the wild type with ultraviolet light and screening for colonies which produce at least 100-fold less aflatoxins than the wild type *A. parasiticus* grown under identical conditions, screening these colonies for hydroxylation of terphenyl compounds and selecting one or more strains which produce terphenyltriols in high yield. The *A. parasiticus* strain of the present invention, isolated by this procedure, produces no detectable aflatoxins (i.e., less than 20 ppb.) and produces a yield of terphenyltriols at least 90% as great as that obtained using the parent wild type of *A. parasiticus.*

The preparation of m-terphenyltriols and aflatoxin minus fungal strain is illustrated by the following examples. All parts and percentages are by weight unless otherwise specified.

EXAMPLE 1

Spores of *A. parasiticus* strain ATCC 15517 were plated on Sabouraud Dextrose (Difco) with Bacto agar added to 1.5%, and irradiated with a germicidal UV light source at 60 microwatt hours per square centimeter measured at the culture plate surface. Approximately 99% of the irradiated spores failed to germinate. Spores that did germinate were transferred to aflatoxin production plates as described by Lennox and Davis, "Selection of and Complementation Analysis Among Aflatoxin Deficient Mutant of *Aspergillus parasiticus*", *Exp. Myco.*, 8, 192–195 (1983), which description is hereby incorporated by reference. Four colonies were inoculated per plate with a wild-type control at the center. Decreased aflatoxin producers were screened by illuminating the plates with a long-wave UV lamp (366 nm.) and by looking for the absence of a blue halo, which normally surrounds a wild-type colony. Several low-level aflatoxin producers were isolated after screening several thousand colonies that developed from UV-irradiated spores.

Thin layer chromatography and high pressure liquid chromatography were used to detect aflatoxins after extraction from spent media, mycelia or agar plates. Aflatoxin standards (Sigma) were always run in parallel. These analyses showed that strain JS 1-89 produced no detectable aflatoxins. The hydroxylation activity of strain JS 1-89 was comparable to wild type isolates.

EXAMPLE 2

The spore production agar employed in this example was prepared by dissolving in water 218 g. of sorbitol, 5 g. of yeast extract, 20 ml. of Aspergillus minimal salts solution, 1 ml. of trace elements solution, 10 g. of glucose and 15 g. of Bacto-Agar, autoclaving the solution and combining it with 10 ml. of 0.2M magnesium sulfate heptahydrate solution. The Aspergillus minimal salts solution was prepared by dissolving in 1 liter of water 300 g. of sodium nitrate, 75 g. of potassium dihydrogen phosphate and 25 g. of potassium chloride and adjusting the pH to 6.5 by addition of sodium hydroxide. The trace elements solution was prepared by dissolving in 1 liter of water 500 mg. of boric acid, 40 mg. of cupric sulfate pentahydrate, 100 mg. of potassium iodide, 200 mg. of ferric chloride monohydrate, 160 mg. of molybdic acid and 400 mg. of zinc sulfate heptahydrate. The spore harvesting buffer was an aqueous solution of 1% sodium chloride, 0.1% Triton X-100 surfactant and 20% glycerol.

A stock of spores of strain JS 1-89 was prepared by inoculating spore production agar with $5\times10^5$ spores of the strain and incubating for two days at 30° C., then at room temperature until a heavy "lawn" of green spores had developed. They were suspended in spore harvesting buffer, spun down, resuspended in fresh buffer, diluted to the desired concentration and stored at −80° C. An inoculum culture was prepared by charging five 2-liter baffled Erlenmeyer flasks with 400 ml. of sterile Sabouraud Dextrose, inoculating with JS 1-89 spores at $6\times10^8$ spores per flask and incubating for 24 hours at 37° C.

A 400-liter straight-sided polyethylene tank fitted with a motor-driven stirrer was chemically sterilized with sodium hypochlorite and isopropyl alcohol, charged with 300 liters of an aqueous solution comprising 22 g./l. Karo corn syrup, 43 g./l. Argo Steepwater E801 corn steep liquor and 20 mg./l. tetracycline hydrochloride as a bacterial suppressor, inoculated with the contents of the spore germination flasks, and sparged with sterilized air at 37° C. for 24 hours. There were then added, with stirring, 600 grams of 2'-hydroxy-m-terphenyl, 1200 grams of Triton X-100 surfactant and 15 grams of 4,4'-biphenol as a promoter. Air sparging was continued as an aqueous solution containing 300 g./l. of corn syrup was added at 0.05 g./l./hr. of corn syrup for the first 65 hours, 0.12 g./l./hr. for the next 95 hours and 0.008 g./l./hr. until bioconversion was complete. The pH and ammonium ion concentration of the mixture were monitored during the bioconversion.

When bioconversion was complete, the mixture was brought to a pH of 12 and the contents were centrifuged. The solids were reslurried at pH 12 and recentrifuged and the combined liquid phases were acidified to a pH of 7 and extracted with ethyl acetate. The extracts were purified by liquid/liquid extraction and flash chromatography to yield 102 grams of 2',4,4"-m-terphenyltriol. The structure of the product was confirmed by proton and carbon-13 nuclear magnetic resonance and mass spectrometry and it was shown by high pressure liquid chromatography and gas chromatography to be greater than 99% pure.

The branched polycarbonates of this invention may be prepared by conventional interfacial phosgenation methods, as described hereinabove. The m-terphenyltriol is incorporated in the reaction mixture in an amount effective to afford a branched product, typically about 0.2–2.0 mole percent based on dihydroxyaromatic compound. It is also within the scope of the invention to incorporate chain termination agents, typically monohydroxyaromatic compounds such as phenol, t-butylphenol and p-cumylphenol, in the reaction mixture to regulate the molecular weight of the branched polycarbonate. Such chain termination agents are typically present in an amount up to about 5 mole percent based on dihydroxyaromatic compound.

The viscosity properties of branched polycarbonates may be characterized by two parameters, melt index ratio and complex melt viscosity ratio. The melt index ratio is the ratio of melt flow rates at two different shear levels and is a measure of the non-Newtonian property of the copolymer. It is typically less than 1.4 for a linear Newtonian polycarbonate and greater than 1.5 for a branched polycarbonate.

The complex melt viscosity ratio is the ratio of the complex melt viscosity at low shear to that at high shear, as during extrusion, the latter value being taken as 20,000 poise at a shear of 100 radians/sec. This ratio is thus a measure of the shear thinning behavior of the polymer. Experience has taught that good blow molding performance is obtained when the complex melt viscosity ratio is equal to or greater than 3.5.

Complex melt viscosity ratios are determined from the complex viscosities as measured on a Rheometrics Dynamic Spectrometer at three different temperatures, typically 230°, 250° and 270° C. Using these data fitted to the Arrhenius equation, the optimum processing extrusion temperature is calculated; i.e., that temperature at which the melt viscosity is 20,000 poise at 100 radians per second. Then the viscosity at low shear is determined at this temperature. The quotient obtained by dividing the latter viscosity by 20,000 is the complex melt viscosity ratio.

The preparation of the branched polycarbonates of this invention is illustrated by the following examples. All polymer molecular weights were determined by gel permeation chromatography relative to polystyrene.

EXAMPLES 3-4

A 1-liter, 5-necked Morton flask equipped with a condenser cooled with solid carbon dioxide, a pH electrode, a caustic addition port, a mechanical stirrer and a phosgene dip tube was charged with 45.6 grams of bisphenol A, 400 ml. of methylene chloride, 100 ml. of water, a measured amount of phenol, 250 microliters of triethylamine and 239 mg. (0.43 mole percent based on bisphenol A) of 2',4,4''-m-terphenyltriol. The mixture was stirred as phosgene was passed in at 1.25 grams per minute, while the pH was maintained in the range of 10.5-11 by the addition of 50% aqueous sodium hydroxide solution. After 20 minutes of phosgene addition, the contents of the flask were transferred to a separatory funnel and the organic phase was removed and washed twice with aqueous hydrochloric acid solution and four times with water. The washed organic phase was added to four volumes of methanol in a high speed blender, whereupon the desired branched polycarbonate precipitated. It was removed by filtration, washed with water and dried in a vacuum oven at 120° C.

The properties of the branched polycarbonates of this invention are given in the following table, in comparison with a control in which the branching agent (employed at the same mole percentage level) was 1,1,1-tris(4-hydroxyphenyl)ethane.

|  | Example | | Control |
|---|---|---|---|
|  | 3 | 4 |  |
| Phenol, mole % based on bisphenol A | 3.0 | 2.8 | 3.0 |
| Mw | 81,200 | 87,300 | 74,100 |
| Mn | 22,000 | 22,500 | 21,300 |
| Melt index ratio | 3.08 | 3.37 | 3.10 |
| Complex melt viscosity ratio | 4.67 | 5.01 | 4.73 |

What is claimed is:

1. A branched polycarbonate comprising structural units of the formula

wherein $R^1$ is a divalent organic radical, and branching units of the formula

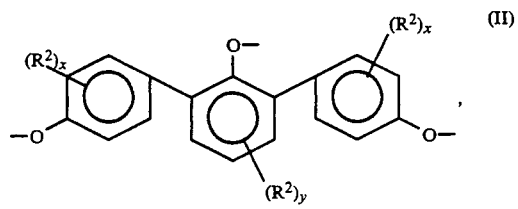

wherein each $R^2$ is a substantially inert substituent, x is 0–4 and y is 0–3.

2. A polycarbonate according to claim 1 wherein $R^1$ has the formula

wherein each of $A^1$ and $A^2$ is a monocyclic divalent aromatic radical and Y is a bridging radical in which one or two atoms separate $A^1$ from $A^2$.

3. A polycarbonate according to claim 2 wherein x and y are each 0.

4. A polycarbonate according to claim 2 wherein each of $A^1$ and $A^2$ is p-phenylene and Y is isopropylidene.

5. A polycarbonate according to claim 4 wherein x and y are each 0.

* * * * *